(12) United States Patent
Hartoumbekis

(10) Patent No.: US 9,592,067 B2
(45) Date of Patent: Mar. 14, 2017

(54) SPECIMEN RETRIEVAL DEVICE INCLUDING A REUSABLE SHAFT WITH INTERCHANGEABLE POUCH

(71) Applicant: Covidien LP, Mansfield, MA (US)

(72) Inventor: Elias Hartoumbekis, New Haven, CT (US)

(73) Assignee: Covidien LP, Mansfield, MA (US)

( * ) Notice: Subject to any disclaimer, the term of this patent is extended or adjusted under 35 U.S.C. 154(b) by 358 days.

(21) Appl. No.: 14/247,297

(22) Filed: Apr. 8, 2014

(65) Prior Publication Data

US 2014/0371759 A1 Dec. 18, 2014

Related U.S. Application Data

(60) Provisional application No. 61/834,923, filed on Jun. 14, 2013.

(51) Int. Cl.
*A61B 17/24* (2006.01)
*A61B 17/221* (2006.01)
*A61B 17/00* (2006.01)

(52) U.S. Cl.
CPC ...... *A61B 17/221* (2013.01); *A61B 17/00234* (2013.01); *A61B 2017/0046* (2013.01); *A61B 2017/00287* (2013.01)

(58) Field of Classification Search
CPC ............ A61B 17/221; A61B 17/00234; A61B 2017/00287; A61B 2017/0046
See application file for complete search history.

(56) References Cited

U.S. PATENT DOCUMENTS

| 30,471 A | 10/1860 | Dudley |
| 35,164 A | 5/1862 | Logan et al. |
| 156,477 A | 11/1874 | Bradford |
| 1,609,014 A | 11/1926 | Dowd |
| 3,800,781 A | 4/1974 | Zalucki |
| 4,557,255 A | 12/1985 | Goodman |

(Continued)

FOREIGN PATENT DOCUMENTS

| DE | 3542667 A1 | 6/1986 |
| DE | 8435489 U1 | 8/1986 |

(Continued)

OTHER PUBLICATIONS

European Search Report EP 14172391.6 dated Oct. 9, 2014.

(Continued)

*Primary Examiner* — Todd J Scherbel
*Assistant Examiner* — Son Dang

(57) ABSTRACT

A specimen retrieval device is provided. The specimen retrieval device includes a housing that includes an outer shaft extending distally therefrom. An inner shaft is disposed within the outer shaft and includes a spring including two or more members. One or both of the members includes a support member interface member. A pouch is releasably couplable to the members and includes a cinch having a proximal end that is passable through the outer shaft for grasping by a user. The pouch includes a pair of openings that lead to a sleeve that is provided on the pouch. Each of the openings is configured to receive a respective one of the members so as to allow the support member interface member on the member(s) to engage a corresponding pocket on the pouch.

19 Claims, 2 Drawing Sheets

(56) References Cited

U.S. PATENT DOCUMENTS

| | | |
|---|---|---|
| 4,611,594 A | 9/1986 | Grayhack et al. |
| 4,744,363 A | 5/1988 | Hasson |
| 4,790,812 A | 12/1988 | Hawkins, Jr. et al. |
| 4,852,586 A | 8/1989 | Haines |
| 4,927,427 A | 5/1990 | Kriauciunas et al. |
| 4,977,903 A | 12/1990 | Haines |
| 4,991,593 A | 2/1991 | LeVahn |
| 4,997,435 A | 3/1991 | Demeter |
| 5,037,379 A | 8/1991 | Clayman et al. |
| 5,074,867 A | 12/1991 | Wilk |
| 5,084,054 A | 1/1992 | Bencini et al. |
| 5,143,082 A | 9/1992 | Kindberg et al. |
| 5,147,371 A | 9/1992 | Washington et al. |
| 5,176,687 A | 1/1993 | Hasson et al. |
| 5,190,542 A | 3/1993 | Nakao et al. |
| 5,190,555 A | 3/1993 | Wetter et al. |
| 5,190,561 A | 3/1993 | Graber |
| 5,192,284 A | 3/1993 | Pleatman |
| 5,192,286 A | 3/1993 | Phan et al. |
| 5,201,740 A | 4/1993 | Nakao et al. |
| 5,215,521 A | 6/1993 | Cochran et al. |
| 5,224,930 A | 7/1993 | Spaeth et al. |
| 5,234,439 A | 8/1993 | Wilk et al. |
| 5,279,539 A | 1/1994 | Bohan et al. |
| 5,312,416 A | 5/1994 | Spaeth et al. |
| 5,330,483 A | 7/1994 | Heaven et al. |
| 5,336,227 A | 8/1994 | Nakao et al. |
| 5,337,754 A | 8/1994 | Heaven et al. |
| 5,341,815 A | 8/1994 | Cofone et al. |
| 5,352,184 A | 10/1994 | Goldberg et al. |
| 5,354,303 A | 10/1994 | Spaeth et al. |
| 5,368,545 A | 11/1994 | Schaller et al. |
| 5,368,597 A | 11/1994 | Pagedas |
| 5,370,647 A | 12/1994 | Graber et al. |
| 5,443,472 A | 8/1995 | Li |
| 5,465,731 A * | 11/1995 | Bell ............... A61B 17/00234 600/37 |
| 5,480,404 A | 1/1996 | Kammerer et al. |
| 5,486,182 A | 1/1996 | Nakao et al. |
| 5,486,183 A * | 1/1996 | Middleman ............ A61B 10/02 606/113 |
| 5,499,988 A | 3/1996 | Espiner et al. |
| 5,524,633 A | 6/1996 | Heaven et al. |
| 5,535,759 A | 7/1996 | Wilk |
| 5,611,803 A | 3/1997 | Heaven et al. |
| 5,618,296 A | 4/1997 | Sorensen et al. |
| 5,630,822 A | 5/1997 | Hermann et al. |
| 5,642,282 A | 6/1997 | Sonehara |
| 5,643,282 A | 7/1997 | Kieturakis |
| 5,643,283 A | 7/1997 | Younker |
| 5,645,083 A | 7/1997 | Essig et al. |
| 5,647,372 A | 7/1997 | Tovey et al. |
| 5,649,902 A | 7/1997 | Yoon |
| 5,658,296 A | 8/1997 | Bates et al. |
| 5,679,423 A | 10/1997 | Shah |
| 5,681,324 A | 10/1997 | Kammerer et al. |
| 5,735,289 A | 4/1998 | Pfeffer et al. |
| 5,755,724 A | 5/1998 | Yoon |
| 5,759,187 A | 6/1998 | Nakao et al. |
| 5,769,794 A | 6/1998 | Conlan et al. |
| 5,785,677 A | 7/1998 | Auweiler |
| 5,788,709 A | 8/1998 | Riek et al. |
| 5,792,145 A | 8/1998 | Bates et al. |
| 5,814,044 A | 9/1998 | Hooven |
| 5,829,440 A | 11/1998 | Broad, Jr. |
| 5,836,953 A | 11/1998 | Yoon |
| 5,853,374 A | 12/1998 | Hart et al. |
| 5,895,392 A | 4/1999 | Riek et al. |
| 5,906,621 A | 5/1999 | Secrest et al. |
| 5,908,429 A | 6/1999 | Yoon |
| 5,957,884 A | 9/1999 | Hooven |
| 5,971,995 A | 10/1999 | Rousseau |
| 5,980,544 A | 11/1999 | Vaitekunas |
| 5,997,547 A | 12/1999 | Nakao et al. |
| 6,004,330 A | 12/1999 | Middleman et al. |
| 6,007,512 A | 12/1999 | Hooven |
| 6,007,546 A | 12/1999 | Snow et al. |
| 6,019,770 A | 2/2000 | Christoudias |
| 6,036,681 A | 3/2000 | Hooven |
| 6,059,793 A | 5/2000 | Pagedas |
| 6,123,701 A | 9/2000 | Nezhat |
| 6,152,932 A | 11/2000 | Ternstrom |
| 6,162,235 A | 12/2000 | Vaitekunas |
| 6,165,121 A | 12/2000 | Alferness |
| 6,168,603 B1 | 1/2001 | Leslie et al. |
| 6,228,095 B1 | 5/2001 | Dennis |
| 6,270,505 B1 | 8/2001 | Yoshida et al. |
| 6,277,083 B1 | 8/2001 | Eggers et al. |
| 6,280,450 B1 | 8/2001 | McGuckin, Jr. |
| 6,344,026 B1 | 2/2002 | Burbank et al. |
| 6,348,056 B1 | 2/2002 | Bates et al. |
| 6,350,266 B1 | 2/2002 | White et al. |
| 6,350,267 B1 | 2/2002 | Stefanchik |
| 6,383,195 B1 | 5/2002 | Richard |
| 6,383,196 B1 | 5/2002 | Leslie et al. |
| 6,383,197 B1 | 5/2002 | Conlon et al. |
| 6,406,440 B1 | 6/2002 | Stefanchik |
| 6,409,733 B1 | 6/2002 | Conlon et al. |
| 6,419,639 B2 | 7/2002 | Walther et al. |
| 6,447,523 B1 | 9/2002 | Middleman et al. |
| 6,471,659 B2 | 10/2002 | Eggers et al. |
| 6,506,166 B1 | 1/2003 | Hendler et al. |
| 6,508,773 B2 | 1/2003 | Burbank et al. |
| 6,537,273 B1 | 3/2003 | Sosiak et al. |
| 6,589,252 B2 | 7/2003 | McGuckin, Jr. |
| 6,752,811 B2 | 6/2004 | Chu et al. |
| 6,755,779 B2 | 6/2004 | Vanden Hoek et al. |
| 6,780,193 B2 | 8/2004 | Leslie et al. |
| 6,805,699 B2 | 10/2004 | Shimm |
| 6,840,948 B2 | 1/2005 | Albrecht et al. |
| 6,872,211 B2 | 3/2005 | White et al. |
| 6,887,255 B2 | 5/2005 | Shimm |
| 6,971,988 B2 | 12/2005 | Orban, III |
| 6,994,696 B2 | 2/2006 | Suga |
| 7,052,454 B2 | 5/2006 | Taylor |
| 7,052,501 B2 | 5/2006 | McGuckin, Jr. |
| 7,090,637 B2 | 8/2006 | Danitz et al. |
| 7,115,125 B2 | 10/2006 | Nakao et al. |
| 7,270,663 B2 | 9/2007 | Nakao |
| 7,273,488 B2 | 9/2007 | Nakamura et al. |
| 7,410,491 B2 | 8/2008 | Hopkins et al. |
| 7,547,310 B2 | 6/2009 | Whitfield |
| 7,670,346 B2 | 3/2010 | Whitfield |
| 7,762,959 B2 | 7/2010 | Bilsbury |
| 7,819,121 B2 | 10/2010 | Amer |
| 7,837,612 B2 | 11/2010 | Gill et al. |
| 8,057,485 B2 | 11/2011 | Hollis et al. |
| 8,579,914 B2 | 11/2013 | Menn et al. |
| 2002/0068943 A1 | 6/2002 | Chu et al. |
| 2002/0082516 A1 | 6/2002 | Stefanchik |
| 2003/0073970 A1 | 4/2003 | Suga |
| 2003/0100909 A1 | 5/2003 | Suzuki |
| 2003/0100919 A1 | 5/2003 | Hopkins et al. |
| 2003/0199915 A1 | 10/2003 | Shimm |
| 2003/0216773 A1 | 11/2003 | Shimm |
| 2004/0097960 A1 | 5/2004 | Terachi et al. |
| 2004/0138587 A1 | 7/2004 | Lyons |
| 2005/0085808 A1 | 4/2005 | Nakao |
| 2005/0165411 A1 | 7/2005 | Orban |
| 2005/0267492 A1 | 12/2005 | Poncet et al. |
| 2006/0030750 A1 | 2/2006 | Amer |
| 2006/0052799 A1 | 3/2006 | Middleman et al. |
| 2006/0058776 A1 | 3/2006 | Bilsbury |
| 2006/0169287 A1 | 8/2006 | Harrison et al. |
| 2006/0200169 A1 | 9/2006 | Sniffin |
| 2006/0200170 A1 | 9/2006 | Aranyi |
| 2006/0229639 A1 | 10/2006 | Whitfield |
| 2006/0229640 A1 | 10/2006 | Whitfield |
| 2007/0016224 A1 | 1/2007 | Nakao |
| 2007/0016225 A1 | 1/2007 | Nakao |
| 2007/0073251 A1 | 3/2007 | Zhou et al. |
| 2007/0088370 A1 | 4/2007 | Kahle et al. |
| 2007/0135780 A1 | 6/2007 | Pagedas |
| 2007/0135781 A1 | 6/2007 | Hart |

(56) References Cited

U.S. PATENT DOCUMENTS

| | | | |
|---|---|---|---|
| 2007/0186935 A1 | 8/2007 | Wang et al. | |
| 2008/0188766 A1 | 8/2008 | Gertner | |
| 2008/0221588 A1 | 9/2008 | Hollis et al. | |
| 2008/0234696 A1* | 9/2008 | Taylor | A61B 17/00234 606/114 |
| 2008/0300621 A1 | 12/2008 | Hopkins et al. | |
| 2008/0312496 A1 | 12/2008 | Zwolinski | |
| 2009/0082779 A1 | 3/2009 | Nakao | |
| 2009/0182292 A1 | 7/2009 | Egle et al. | |
| 2009/0192510 A1 | 7/2009 | Bahney | |
| 2009/0240238 A1 | 9/2009 | Grodrian et al. | |
| 2010/0000471 A1 | 1/2010 | Hibbard | |
| 2011/0184434 A1 | 7/2011 | Parihar et al. | |
| 2011/0184436 A1 | 7/2011 | Shelton, IV et al. | |
| 2011/0190781 A1 | 8/2011 | Collier et al. | |
| 2011/0299799 A1 | 12/2011 | Towe | |
| 2012/0046667 A1 | 2/2012 | Cherry et al. | |
| 2012/0083795 A1 | 4/2012 | Fleming et al. | |
| 2012/0203241 A1 | 8/2012 | Williamson, IV | |
| 2013/0023895 A1 | 1/2013 | Saleh | |
| 2013/0103402 A1 | 4/2013 | Chopra et al. | |
| 2015/0289864 A1* | 10/2015 | Holsten | A61B 17/00234 606/114 |

FOREIGN PATENT DOCUMENTS

| | | |
|---|---|---|
| DE | 4204210 A1 | 8/1992 |
| DE | 19624826 A1 | 1/1998 |
| EP | 0930047 A1 | 7/1999 |
| EP | 0947166 A2 | 10/1999 |
| EP | 1685802 A1 | 8/2006 |
| EP | 1707126 A1 | 10/2006 |
| EP | 2005900 A2 | 12/2008 |
| EP | 2184014 A2 | 5/2010 |
| EP | 2497429 A1 | 9/2012 |
| EP | 2583629 A2 | 4/2013 |
| FR | 1272412 A | 9/1961 |
| GB | 246009 A | 1/1926 |
| WO | 9315675 A1 | 8/1993 |
| WO | 9509666 A1 | 4/1995 |
| WO | 01/35831 A1 | 5/2001 |
| WO | 2004002334 A1 | 1/2004 |
| WO | 2004/112571 A2 | 12/2004 |
| WO | 2005/112783 A1 | 12/2005 |
| WO | 2006/110733 | 10/2006 |
| WO | 2007/048078 A1 | 4/2007 |
| WO | 2007/048085 A2 | 4/2007 |
| WO | 2008/114234 A2 | 9/2008 |
| WO | 2009/149146 A1 | 12/2009 |
| WO | 2011/090862 A2 | 7/2011 |

OTHER PUBLICATIONS

European Search Report EP 12191639.9 dated Feb. 20, 2013.
European Search Report EP 11250837.9 dated Sep. 10, 2013.
European Search Report EP 11250838.7 dated Sep. 10, 2013.
European Search Report EP 13170118.7 dated Dec. 5, 2013.
European Search Report EP 12165852 dated Jun. 20, 2012.
http://www.biomaterials.org/week/bio17.cfm, definition and examples of hydrogels.
European Search Report EP 12150271 dated Jan. 14, 2013.
European Search Report EP 12193450 dated Feb. 27, 2013.
European Search Report EP 12189517.1 dated Mar. 6, 2013.
European Search Report EP 12158873 dated Jul. 19, 2012.
European Search Report EP 11250836 dated Sep. 12, 2013.
European Office Action corresponding to counterpart Int'l Application No. EP 14172391.6 dated Nov. 2, 2015.
European Office Action corresponding to counterpart Int'l Appln. No. EP 14 17 2391.6, dated May 2, 2016.

* cited by examiner

SPECIMEN RETRIEVAL DEVICE INCLUDING A REUSABLE SHAFT WITH INTERCHANGEABLE POUCH

CROSS-REFERENCE TO RELATED APPLICATIONS

This application claims the benefit of and priority to U.S. Provisional Patent Application No. 61/834,923, filed Jun. 14, 2013, the entire disclosure of which is incorporated by reference herein.

BACKGROUND

Technical Field

The present disclosure relates to a specimen retrieval device. More particularly, the present disclosure relates to a specimen retrieval device including a reusable shaft with an interchangeable pouch.

Background of Related Art

Laparoscopic and endoscopic surgical procedures are minimally invasive procedures in which operations are carried out within the body by means of elongated instruments inserted through small entrance or access openings in the body, e.g., an opening defined by a natural passageway of the body, an opening created by a tissue piercing instrument (e.g., a trocar), etc.

Minimally invasive procedures are often used to partially or totally remove body tissue or organs from the interior of the body, e.g. nephrectomy, cholecystectomy, duodenectomy, ileectomy, jejunectomy and other such procedures. During such procedures, it is common that affected tissue or organs must be removed via the access opening in the skin, or through a cannula. Various types of entrapment devices are known in the art to facilitate this procedure.

Conventional entrapment devices typically include an elongated applicator including a handle at a proximal end that is operable to deploy a pouch or other suitable device from a distal end of the applicator. The pouch may be perforated and releasably coupled to a spring member along the perforations. As a result of the perforations on the pouch, the pouch may be detached from the spring member by tearing along the perforations. A top portion of the pouch remains on the spring after the pouch is detached therefrom; this top portion is, typically, not configured for removal from the inner shaft. Accordingly, the inner shaft is not reusable and therefore discarded.

SUMMARY

As can be appreciated, a specimen retrieval device including a reusable shaft with an interchangeable pouch may prove useful in the surgical arena.

An aspect of the instant disclosure provides a specimen retrieval device. The specimen retrieval device includes a housing that includes an outer shaft extending distally therefrom. An inner shaft is disposed within the outer shaft and includes a spring including two or more members. The inner shaft may include a finger ring at a proximal end. One or both of the members includes a support member interface member. A pouch is releasably couplable to the members and includes a cinch having a proximal end that is passable through the outer shaft for grasping by a user. The pouch includes a pair of openings that lead to a sleeve that is provided on the pouch. Each of the openings is configured to receive a respective one of the members so as to allow the support member interface member on the member(s) to engage a corresponding pouch interface member, e.g., a pocket on the pouch. The support member interface members may be in the form of a tab portion.

A distal end of the cinch may be secured to a perforated portion of the pouch. A top portion of the pouch may be located adjacent the perforated portion of the pouch and may be compressible for loading the pouch onto the members. The proximal end of the cinch may be coupled to a suture guide having an elongated configuration. The suture guide may be receivable through one or more lumens extending through the outer shaft. The lumen(s) may be further defined by a first lumen that is configured to receive the inner shaft and a second lumen extending parallel to the first lumen configured to receive the suture guide.

Each of the members may include a support member interface member and the pouch may include two corresponding pockets that are configured to engage a respective one of the support member interface members.

An aspect of the instant disclosure provides a specimen retrieval device. The specimen retrieval device includes a housing that includes an outer shaft extending distally therefrom. An inner shaft is disposed within the outer shaft and includes a spring including two or more members. The inner shaft may include a finger ring at a proximal end. One or both of the members includes a support member interface member. A pouch is releasably couplable to the members. The pouch may include a compressible top portion that is moveable from an uncompressed condition for defining an opening of the pouch to a compressed condition for allowing coupling of the pouch onto the members. The pouch includes a pair of openings that lead to a sleeve that is provided on the pouch. Each of the openings is configured to receive a respective one of the members so as to allow the support member interface member on the member(s) to engage a corresponding pocket on the pouch. Retraction of the inner shaft within the outer shaft causes the members to compress toward one another so as to allow a user to couple the pouch onto the members.

The pouch may include a cinch having a proximal end that is passable through the outer shaft for grasping by a user. A distal end of the cinch is secured to a perforated portion of pouch.

The support member interface member on the member(s) may be in the form of a tab portion. The proximal end of the cinch is coupled to a suture guide having an elongated configuration. The suture guide may be receivable through one or more lumens that extend through the outer shaft. The suture guide is weighted to facilitate moving the suture guide through the second lumen. The lumen may be further defined by a first lumen that is configured to receive the inner shaft and a second lumen extending parallel to the first lumen configured to receive the suture guide.

Each of the members may include a support member interface member and the pouch may include two corresponding pockets that are configured to engage a respective one of the support member interface members.

An aspect of the instant disclosure provides a specimen retrieval device. The specimen retrieval device includes a housing that includes an outer shaft extending distally therefrom. An inner shaft is disposed within the outer shaft and includes a spring including two or more support members. The inner shaft may include a finger ring at a proximal end. One or both of the support members includes a support member interface member. A pouch is releasably couplable to the support members. The pouch may include a compressible top portion that is moveable from an uncompressed condition for defining an opening of the pouch to a compressed condition for allowing coupling of the pouch onto the support members. The pouch includes a pair of openings that lead to a sleeve that is provided on the pouch. Each of the openings is configured to receive a respective one of the support members so as to allow the support member interface member on the support member(s) to engage a corresponding pocket on the pouch. Retraction of the inner shaft within the outer shaft causes the support members to compress toward one another so as to allow a user to couple the pouch onto the support members when the pouch is in the compressed condition.

BRIEF DESCRIPTION OF THE DRAWINGS

Embodiments of the presently disclosed specimen retrieval device are described hereinbelow with reference to the drawings wherein.

DETAILED DESCRIPTION OF THE EMBODIMENTS

Figure 1:
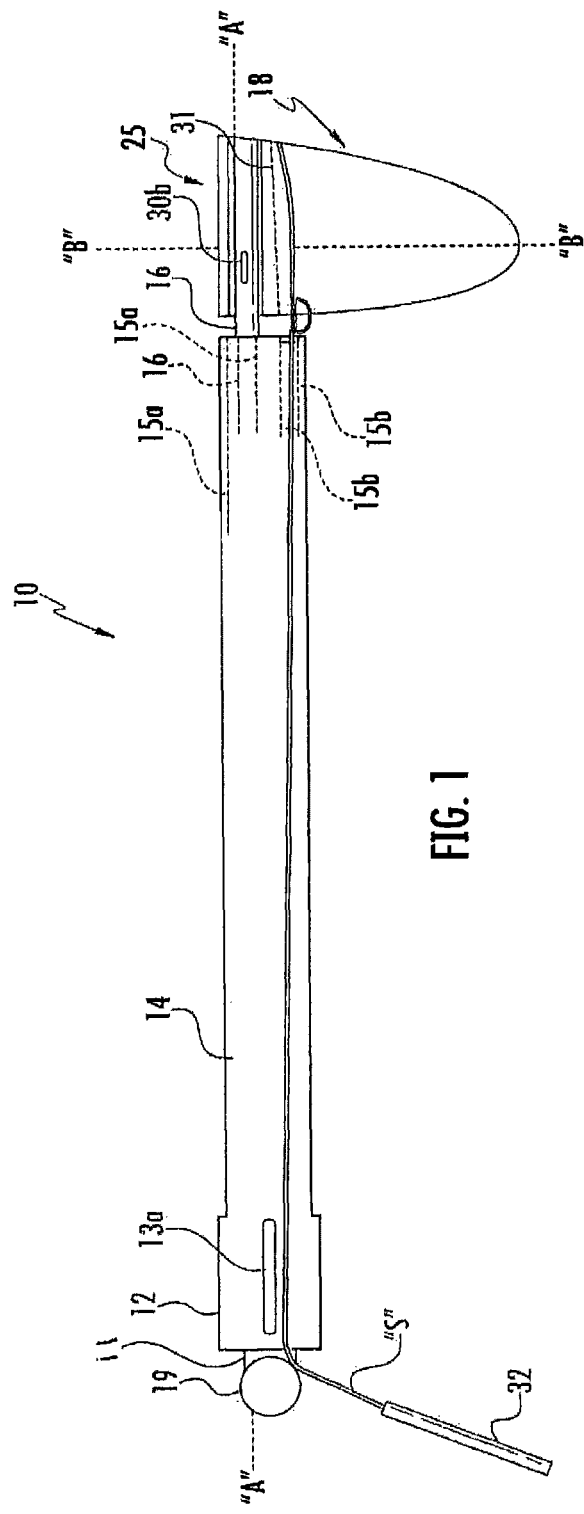
FIG. 1 is a side view of a specimen retrieval device including a pouch coupled thereto in accordance with an embodiment of the present disclosure.

Embodiments of the present disclosure will now be described in detail with reference to the drawings, in which like reference numerals designate identical or corresponding elements in each of the several views. As used herein, the term distal refers to the portion of the instrument which is farthest from the user, while the term proximal refers to that portion of the instrument which is closest to the user. In the following description, well-known functions or constructions are not described in detail to avoid obscuring the present disclosure in unnecessary detail.

As used herein with reference to the present disclosure, the terms laparoscopic and endoscopic are interchangeable and refer to instruments having a relatively narrow operating portion for insertion into a cannula or a small incision in the skin. They also refer to minimally invasive surgical procedures. It is believed that the present disclosure may find use in any procedure where access to the interior of the body is limited to a relatively small incision, with or without the use of a cannula as in minimally invasive procedures.

Figure 2:
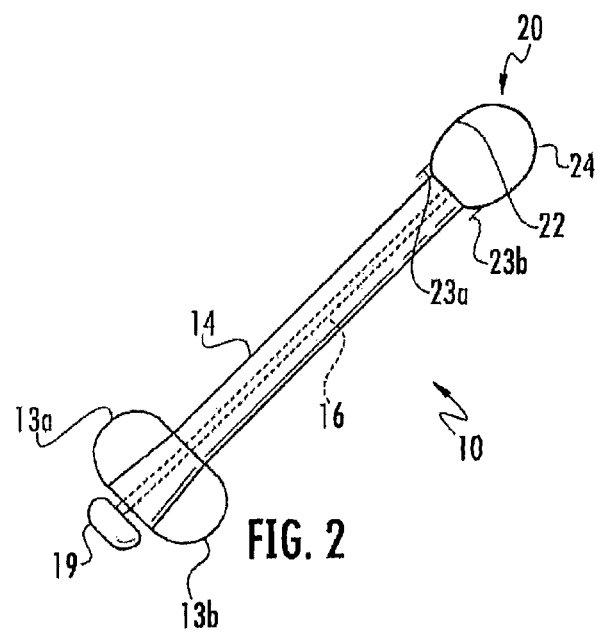
FIG. 2 is a top, elevational view of the specimen retrieval device shown in FIG. 1 without the pouch coupled thereto.
Figure 3:
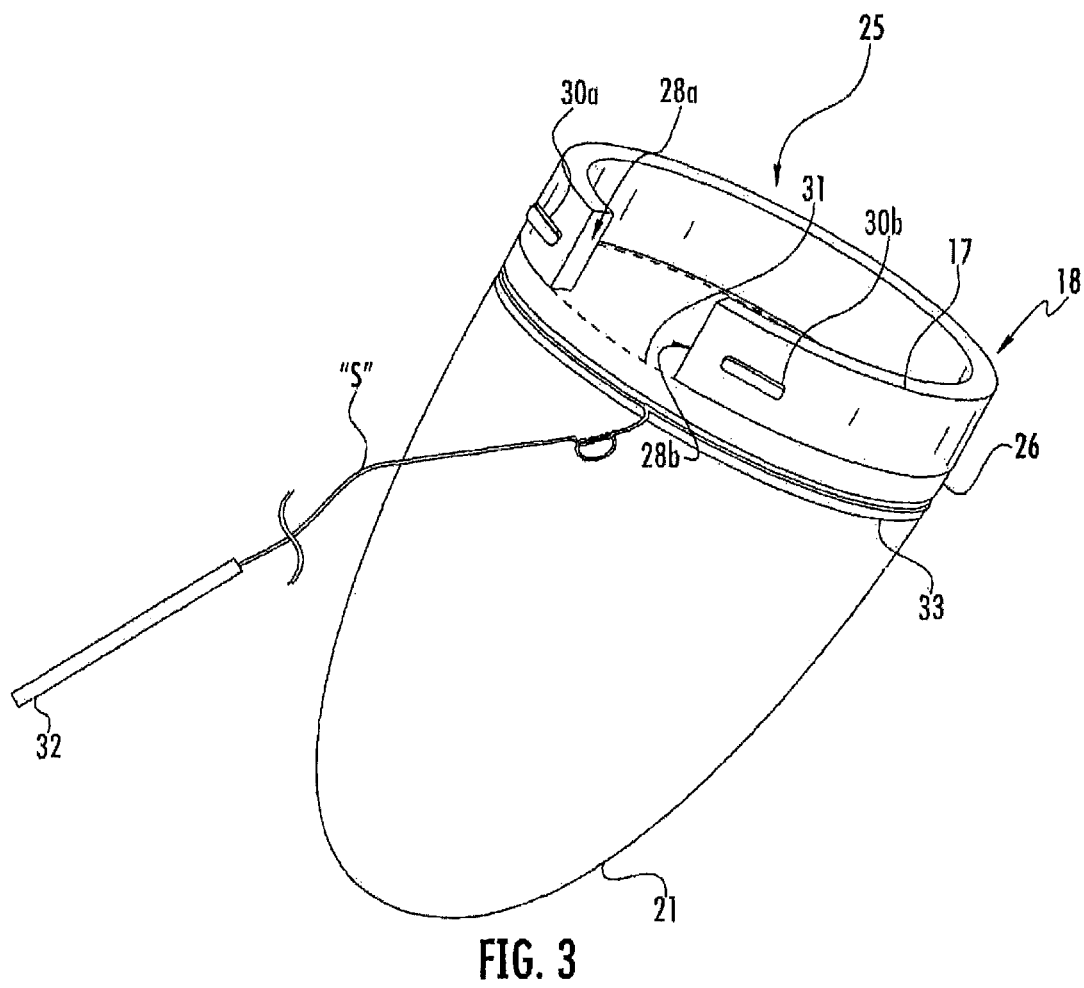
FIG. 3 is a perspective view of the pouch shown in FIG. 1.

With reference to FIGS. 1-3, and initially with reference to FIG. 1, a specimen retrieval device 10 according to an embodiment of the present disclosure is illustrated. Specimen retrieval device 10 includes a housing 12, an outer shaft 14 and an inner shaft 16 (inner shaft 16 is shown in phantom in FIG. 1). Specimen retrieval device 10 (and components associated therewith) may be formed from any suitable biocompatible material, e.g., plastic. In an embodiment, an injection molding manufacturing process may be utilized to form housing 12, outer shaft 14 and inner shaft 16.

Continuing with reference to FIG. 1, housing 12 includes a generally elongated configuration and may be formed as a unitary component or as two separate half components that are coupled to one another by one or more suitable coupling methods (e.g., ultrasonic welding, one or more suitable adhesives). In the latter instance, an indent/detent configuration (not explicitly shown) may be utilized to facilitate coupling the two separate half components. Housing 12 includes a pair of opposing lateral extensions 13a, 13b that may serve as a handle for a user to grasp to facilitate manipulation of specimen retrieval device 10 (FIGS. 1 and 2).

Outer shaft 14 extends distally from housing 12 and includes a generally tubular configuration having a longitudinal axis "A-A" defined therethrough. Longitudinal axis "A-A" is oriented in a different, e.g., a substantially perpendicular or orthogonal direction, with respect to a longitudinal axis "B-B" that is defined through a pouch 18 when the pouch 18 is coupled to the inner shaft 16 and in an open configuration (FIG. 1).

Outer shaft 14 is dimensioned for insertion through a trocar cannula (or natural body orifice) for endoscopic or laparoscopic procedures. Outer shaft 14 operably couples to housing 12 via one or more suitable coupling methods (e.g., adhesives, ultrasonic welding, etc.). Outer shaft 14, however, may be monolithically formed with housing 12.

Outer shaft 14 includes a first lumen 15a and a second lumen 15b (shown in phantom in FIG. 1). First lumen 15a extends along the length of the outer shaft and is configured to support the inner shaft 16 for allowing translation of the inner shaft 16 within the first lumen 15a. Second lumen 15b extends along the length of the outer shaft 14 and is oriented parallel with respect to the first lumen 15a. Second lumen 15b is configured to receive a cinch of the pouch 18 as the pouch 18 is being coupled to the inner shaft 16, as will be discussed in greater detail below.

Inner shaft 16 includes a generally elongated configuration and is translatable within outer shaft 14 to move pouch 18 adjacent tissue of interest. A proximal end 11 of the inner shaft 16 includes a finger loop 19 that is configured to receive a finger of a clinician.

A distal end of the inner shaft 16 includes a support member, which can be in the form of spring 20 (or other suitable device), via one via one or more suitable coupling methods (FIGS. 1 and 2). In the illustrated embodiment, for example, the distal end of the inner shaft 16 is overmolded to the proximal end of spring 20. Other coupling methods may also be utilized to couple spring 20 to the distal end of the inner shaft 16. For example, one or more pins, rivets or the like may be utilized to couple the proximal end of the spring 20 to the distal end of the inner shaft 16.

Referring to FIG. 2, the spring 20 includes two flexible or resilient members 22 and 24 that form an open fork configuration. The resilient members 22, 24 are configured to move from a stressed or non-expanded state (not explicitly shown) to an unstressed or expanded state. Specifically, when a user moves finger loop 19 proximally, the inner shaft 16 moves proximally within the first lumen 15a and the resilient members 22, 24 contact an interior surface thereof (e.g., at the distal end of the outer shaft 14). Continued proximal movement of the inner shaft 16 within the first lumen 15a approximates the resilient members 22, 24 toward one another so that the resilient members 22, 24 become oriented substantially parallel to one another. With the resilient members 22, 24 in this position, a user can releasably couple the pouch 18 to the resilient members 22, 24 of the spring 20.

Each of the resilient members 22, 24 includes a support member interface member in the form of tabs 23a, 23b that are configured to secure the pouch 18 to the resilient members 22, 24 of the spring 20; other support member interface members may also be utilized. For example, the support member interface members may be in the form of detents, hooks, protrusions, and the like. Once the pouch 18 is secured to the resilient members 22, 24, the resilient members 22, 24 will automatically assume their unstressed or expanded condition, to collectively form a generally circular or "hoop-like" configuration for supporting a periphery of an opening 25 of pouch 18 (FIGS. 1 and 2).

Referring to FIG. 3, pouch 18 may be made from any suitable biocompatible materials (e.g., nylon) capable of forming an impermeable flexible membrane. Pouch 18 includes a generally tubular or elongated configuration that is defined by an openable and closable upper portion or mouth 26 and closed lower portion 21. Upper portion 26 includes a circumferential sleeve 17. Sleeve 17 may be formed on pouch 18 via folding upper portion 26 into an interior of the pouch 18 and, subsequently, welding the upper portion 26 thereto.

A pair of openings 28a, 28b (opening 28b is not explicitly shown in FIG. 3) that lead to the sleeve 17 are provided on pouch 18. The openings 28a, 28b are configured to receive respective resilient members 22, 24 of the spring 20 to allow a clinician to slide the sleeve 17 over the resilient members 22, 24. Specifically, when the resilient members 22, 24 are in the stressed state (e.g., the resilient members 22, 24 are approximated toward one another), a clinician may slide the sleeve 17 over the resilient members 22, 24 until the tabs 23a, 23b engage respective pockets 30a, 30b that are provided on the upper portion 26 adjacent the sleeve 17. Once the tabs 23a, 23b engage the pockets 30a, 30b, a clinician can move the inner shaft 16 including the resilient members 22, 24 of the spring 20 distally. Continued distal movement of the inner shaft 16 results in the resilient members 22, 24 automatically moving back to the unstressed configuration, which, in turn, places the pouch 18 in an open configuration for receiving tissue.

A perforated portion 31 of the pouch 18 is provided between the sleeve 17 and a channel 33 that extends circumferentially along the pouch 18. Channel 33 includes a portion of the cinch (e.g., a suture "S," thread, wire, cable or the like) therein that is utilized to cinch the pouch 18 after tissue is positioned within the pouch 18.

Specifically, a distal end of the suture "S" couples to pouch 18 within the channel 33 via one or more suitable coupling methods, e.g., adhesive, welding, etc., and a proximal end of the suture "S" couples to a suture guide 32 that is positionable within the second lumen 15b of the outer shaft 14. The suture guide 32 is insertable through a distal end of the second lumen 15b and is slidable along an interior surface of the second lumen 15b to exit the proximal end of the second lumen 15b. In the illustrated embodiment, the suture guide 32 is weighted to allow the suture guide 32 to slide through the second lumen 15b after the suture guide 32 is inserted into the second lumen 15b and when a clinician moves the distal end of the outer shaft 14 above the longitudinal axis "A-A" (e.g., moves the distal end of the outer shaft 14 in a generally upright configuration).

In use, a clinician can move the inner shaft 16 proximally to retract the spring 20 and resilient members 22, 24 such that the resilient members 22, 24 move toward one another in a manner as described above. Thereafter, the resilient members 22, 24 of the spring 20 may be inserted into the respective openings 28a, 28b of the sleeve 17 and the pouch 18 may be slid onto the spring 20 (or vice versa) until such time that the tabs 23a, 23b on the resilient members 22, 24 engage the pockets 30a, 30b on the sleeve 17.

Once the tabs 23a, 23b engage the pockets 30a, 30b, a clinician can then insert the suture guide 32 into the second lumen 15b of the outer shaft 14. In embodiments, a clinician may raise the outer shaft 14 in a manner as described above to slide the suture guide 32 through the second lumen 15b so that the suture guide 32 exits the proximal end of the second lumen 15b for grasping by the clinician. As can be appreciated, the suture guide 32 may be inserted through the second lumen 15b first and then the pouch 18 can be coupled to the spring 20.

After the pouch 18 is coupled to the spring 20, tissue can be positioned within the pouch 18. Thereafter, a clinician can grasp the suture guide 32 and pull it proximally, which, in turn, will close the pouch 18 and tear the pouch 18 along the perforated portion 31 leaving the sleeve 17 still coupled to the resilient members 22, 24. The suture "S" can then be cut and the inner and outer shafts 16, 14, respectively, may be removed from the patient. The cinched pouch 18 can then be removed from the patient.

In the instance, where another pouch 18 needs to be installed, the sleeve 17 of the upper portion 26 of the pouch 18 may be removed from the resilient members 22, 24 and a new pouch 18 may be coupled to the spring 20 in a manner as described above. As can be appreciated, the new pouch 18 can be coupled to the spring 20 inside or outside the body cavity of a patient.

Unlike conventional specimen retrieval devices, the inner shaft 16 of the specimen retrieval device 10 can be coupled to subsequent pouches 18 and utilized to remove additional tissue of interest. As can be appreciated, this may decrease overall operating costs associated with tissue removal procedures. The specimen retrieval device 10 also allows a surgeon to remove multiple tissue specimens using a single instrument; thus, reducing waste.

From the foregoing and with reference to the various figure drawings, those skilled in the art will appreciate that certain modifications can also be made to the present disclosure without departing from the scope of the same. For example, a cutting mechanism (not shown) may be a part of the housing 12 and/or finger loop 19 and may be configured to sever suture "S" after tissue is positioned within pouch 18 and pouch 18 is closed and removed along the perforation.

In embodiments, the upper portion 26 may be formed from a compressible material that allows the upper portion 26 of the pouch 18 to move between a compressed condition and a non-compressed condition. In this embodiment, a clinician may squeeze the upper portion 26 to compress the upper portion 26 and position the openings 28a, 28b for receipt of the resilient members 22, 24. That is, in the compressed condition, the openings 28a, 28b will be oriented substantially parallel to one another and in placed in general alignment with the corresponding resilient members 22, 24. As can be appreciated, this may facilitate coupling the pouch 18 to the spring 20.

Moreover, in embodiments, the tabs 23a, 23b of the resilient members 22, 24 may be omitted. Specifically, the pouch 18 may be provided with a proximal coupling portion (not shown) that has an opening or aperture which engages a retention pin that may be provided at a distal end of the inner shaft 16. In this embodiment, the inner shaft 16 has near its distal end a notch which defines a proximal notch face and a distal notch face.

Resilient members 22, 24 may be fed through the sleeve 17 of the pouch 18. The retention pin may be extended fully between the notch faces such that the pouch 18 is attached to the distal end of the inner shaft 16 and will not inadvertently become disengaged therefrom.

After the pouch 18 is coupled to the spring 20, tissue can be positioned within the pouch 18. Thereafter, a clinician can grasp the suture guide 32 and pull it proximally, which, in turn, will close the pouch 18 and tear the pouch 18 along the perforated portion 31 leaving the sleeve 17 still coupled to the resilient members 22, 24. The suture "S" can then be cut and the inner and outer shafts 16, 14, respectively, may be removed from the patient. The cinched pouch 18 can then be removed from the patient.

In this embodiment, proximal movement of inner shaft 16 within the first lumen 15a of the outer shaft 14 causes a portion of pouch 18, e.g., sleeve 17, to contact a distal end of outer shaft 14, which, in turn, results in resilient members 22, 24 sliding out from sleeve 17. As can be appreciated, this embodiment is particularly useful when a new pouch 18 needs to be coupled to the spring 20 while the inner and outer shafts 16, 14 are still positioned within a body of a patient.

For a more detailed description of the operative components of the specimen retrieval device 10 that is configured for use with the pouch 18 that does not include the tabs 23a, 23b, reference is made to U.S. Patent Application No. 61/771,129 entitled "Specimen Retrieval Device With Pouch Stop," filed by Malkowski et al. on Mar. 1, 2013 and U.S. Patent Application No. 61/771,138 entitled "Specimen Retrieval Device With Pouch Stop," filed by Malkowski et al. on Mar. 1, 2013, which is hereby incorporated by reference in its entirety.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A specimen retrieval device, comprising:
   a housing including an outer shaft;
   an inner shaft disposed within the outer shaft and including two support members, each of the two support members including a support member interface member; and
   a pouch releasably couplable to the two support members, the pouch including a cinch extending through the outer shaft and having a proximal end positioned to be grasped by a user, the pouch including a sleeve having openings configured to receive the two support members; and
   two pouch interface members, each of the two pouch interface members including a corresponding pocket that is configured to engage a respective one of the support member interface members to prevent inadvertent disengagement of the pouch from the two support members.

2. A specimen retrieval device according to claim 1, wherein each of the support member interface members is in the form of a tab.

3. A specimen retrieval device according to claim 1, wherein a distal end of the cinch is secured to a perforated portion of the pouch.

4. A specimen retrieval device according to claim 3, wherein a top portion of the pouch located adjacent the perforated portion of the pouch is compressible for loading the pouch onto the two support members.

5. A specimen retrieval device according to claim 1, wherein a proximal end of the cinch is coupled to a suture guide having an elongated configuration.

6. A specimen retrieval device according to claim 5, wherein the suture guide is receivable through a lumen extending through the outer shaft.

7. A specimen retrieval device according to claim 6, wherein the at least one lumen is further defined by a first lumen that is configured to receive the inner shaft and a second lumen extending parallel to the first lumen configured to receive the suture guide.

8. A specimen retrieval device according to claim 1, wherein each of the pouch interface members includes a corresponding pocket configured to releasably engage a respective one of the support member interface members.

9. A specimen retrieval device, comprising:
   a housing;
   an outer shaft extending distally from the housing;
   an inner shaft movably disposed within the outer shaft and including two support members, each of the two support members including a support member interface member; and
   a pouch releasably couplable to the two support members, the pouch including a sleeve having two openings, each of the openings being configured to receive a respective one of the two support members, and two pouch interface members, each of the two pouch interface members including a pocket that is configured to engage a respective one of the support member interface members;
   wherein the support member interface members and the pouch interface members are configured such that retraction of the inner shaft within the outer shaft causes the two support members to resiliently compress toward one another so as to allow a user to uncouple the pouch from the two support members.

10. A specimen retrieval device according to claim 9, wherein the pouch includes a cinch having a proximal end that is passable through the outer shaft for grasping by a user.

11. A specimen retrieval device according to claim 9, wherein the support member interface members are in the form of a tab.

12. A specimen retrieval device according to claim 11, wherein the tab includes a resilient portion.

13. A specimen retrieval device according to claim 9, wherein a distal end of the cinch is secured along to a perforated portion of the pouch.

14. A specimen retrieval device according to claim 9, wherein the proximal end of the cinch is coupled to a suture guide.

15. A specimen retrieval device according to claim 14, wherein the suture guide is receivable through a first lumen defined by the outer shaft.

16. A specimen retrieval device according to claim 15, wherein a second lumen is disposed within the first lumen is that is configured to receive the inner shaft.

17. A specimen retrieval device according to claim 15, wherein a channel disposed within the first lumen is configured to receive the suture guide, and the suture guide is weighted to facilitate slidability through the channel.

18. A specimen retrieval device according to claim 9, wherein the inner shaft includes a finger ring at a proximal end.

19. A specimen retrieval device, comprising:
   a housing;
   an outer shaft extending distally from the housing;
   an inner shaft movably disposed within the outer shaft and including a spring including two support members, each of the two support members including a support member interface member; and
   a pouch releasably couplable to the two support members, the pouch including a resilient top portion configured to couple to the two pouch support members, the pouch defining a, passage having openings configured to receive the two support members; and two pouch interface members, each of the pouch interface members including a pocket;

wherein each of the support member interface members of the two support members is configured to engage a corresponding one of the pockets of the two pouch interface members;

wherein retraction of the inner shaft within the outer shaft causes the two support members to resiliently compress toward one another so as to allow a user to couple the pouch onto the two support members.

* * * * *